United States Patent
Kornilov et al.

(12)

(10) Patent No.: US 9,254,081 B2
(45) Date of Patent: Feb. 9, 2016

(54) FITTING GLASSES FRAMES TO A USER

(71) Applicant: Ditto Technologies, Inc., San Francisco, CA (US)

(72) Inventors: Dmitry Kornilov, Saint Petersburg (RU); Sergey Surkov, Foster City, CA (US); Sitaram Bhagavathy, Palo Alto, CA (US)

(73) Assignee: Ditto Technologies, Inc., San Francisco, CA (US)

( * ) Notice: Subject to any disclaimer, the term of this patent is extended or adjusted under 35 U.S.C. 154(b) by 0 days.

(21) Appl. No.: 14/250,203

(22) Filed: Apr. 10, 2014

(65) Prior Publication Data
US 2014/0293220 A1    Oct. 2, 2014

Related U.S. Application Data

(63) Continuation of application No. 13/361,835, filed on Jan. 30, 2012, now Pat. No. 8,733,936.

(51) Int. Cl.
| G02C 3/00 | (2006.01) |
| G02C 7/00 | (2006.01) |
| G02C 7/02 | (2006.01) |
| A61B 3/10 | (2006.01) |
| G02C 13/00 | (2006.01) |
| A61B 3/04 | (2006.01) |

(52) U.S. Cl.
CPC . *A61B 3/10* (2013.01); *G02C 7/027* (2013.01); *G02C 7/028* (2013.01); *G02C 13/003* (2013.01); *A61B 3/04* (2013.01); *G02C 7/02* (2013.01)

(58) Field of Classification Search
CPC ............... G06K 9/78; G06K 9/00248; G06T 2207/30201; G02B 2027/0178; G02C 13/003
USPC ........................................ 351/159.73–159.77
See application file for complete search history.

(56) References Cited

U.S. PATENT DOCUMENTS

| 4,852,184 A | 7/1989 | Tamura et al. |
| 6,736,506 B2 * | 5/2004 | Izumitani et al. ............. 351/204 |
| 7,016,824 B2 | 3/2006 | Waupotitsch et al. |
| 7,292,713 B2 | 11/2007 | Fukuma et al. |
| 8,359,247 B2 | 1/2013 | Vock |
| 2006/0140486 A1 | 6/2006 | Kondo et al. |
| 2010/0179789 A1 | 7/2010 | Sachdeva et al. |
| 2013/0013447 A1 * | 1/2013 | Chityala et al. ............. 705/26.7 |

* cited by examiner

*Primary Examiner* — Mahidere Sahle
(74) *Attorney, Agent, or Firm* — Van Pelt, Yi & James LLP

(57) ABSTRACT

A system for fitting glasses frames to a user is disclosed. The system includes an interface for receiving images of a user's head at different angles. A processor compares user head measurements determined from the images with a database of glasses frame information that includes glasses frame measurements. One or more glasses frames are selected based on the comparison and the selected glasses frames are output.

20 Claims, 11 Drawing Sheets

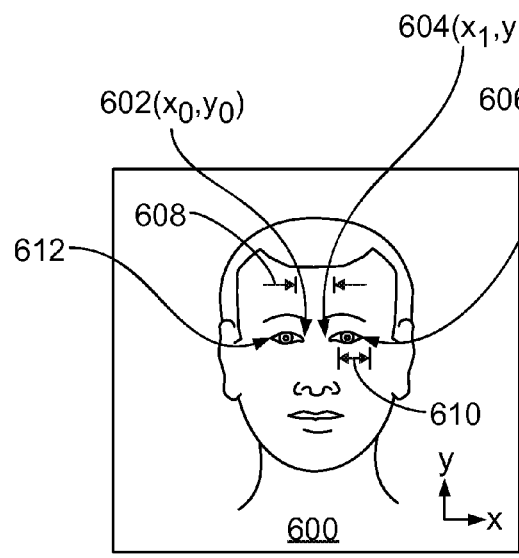
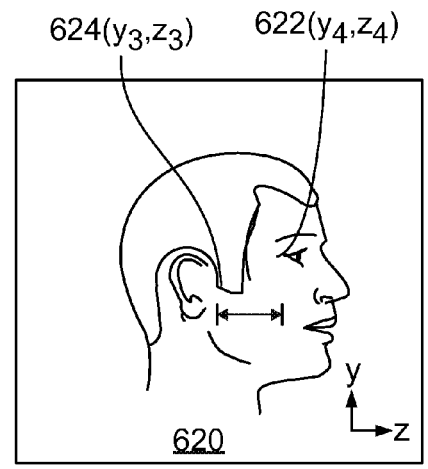
FIG. 6A    FIG. 6B
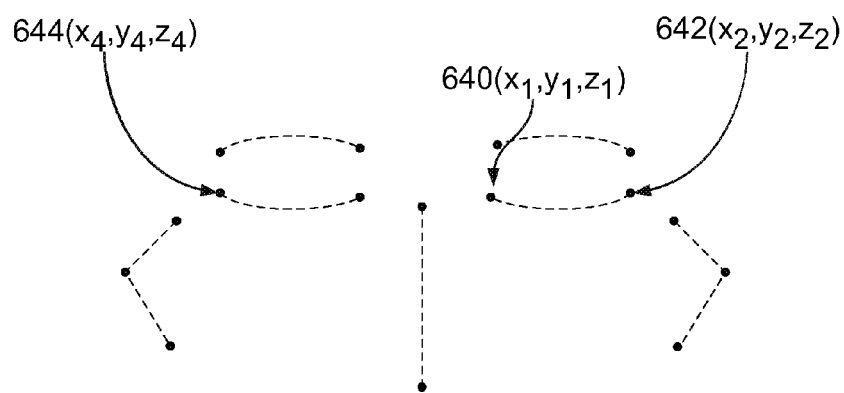
FIG. 6C

| | 910 | 912<br>Name | 914<br>Price | 916<br>Fit Score |
|---|---|---|---|---|
| | | Frame 1 | $99 | 9.6 |
| | | Frame 2 | $120 | 9.5 |
| | | Frame 3 | $200 | 8.0 |

FIG. 9

FITTING GLASSES FRAMES TO A USER

CROSS REFERENCE TO OTHER APPLICATIONS

This application is a continuation of U.S. patent application Ser. No. 13/361,835, entitled FITTING GLASSES FRAMES TO A USER filed Jan. 30, 2012 which is incorporated herein by reference for all purposes.

BACKGROUND OF THE INVENTION

A person seeking to buy glasses usually has to go in person to an optometrist or an eyewear store and try on several glasses frames to see if they fit them. Typically this requires a few hours of browsing through several rows of glasses frames and trying on many pairs of glasses frames, most of the time without prior knowledge of whether a particular glasses frame fit or not. Although glasses frames are designed to fit most people, not all heads are the same size and therefore not all glasses will fit a person. Additionally, glasses frames not only have the functional purpose of correcting the wearer's vision, but also an aesthetic purpose, which adds other factors to the selection process. What is needed is a way to fit glasses frames to people more efficiently.

BRIEF DESCRIPTION OF THE DRAWINGS

Various embodiments of the invention are disclosed in the following detailed description and the accompanying drawings.

FIG. 6A and FIG. 6B illustrate an example of reference points obtained from a set of images/video frames of the user's head.

FIG. 6C is a diagram illustrating the initial 3D model comprising a set of reference points.

FIG. 9 is an illustration of an example of a results list of glasses frames outputted to be displayed.

DETAILED DESCRIPTION

The invention can be implemented in numerous ways, including as a process; an apparatus; a system; a composition of matter; a computer program product embodied on a computer readable storage medium; and/or a processor, such as a processor configured to execute instructions stored on and/or provided by a memory coupled to the processor. In this specification, these implementations, or any other form that the invention may take, may be referred to as techniques. In general, the order of the steps of disclosed processes may be altered within the scope of the invention. Unless stated otherwise, a component such as a processor or a memory described as being configured to perform a task may be implemented as a general component that is temporarily configured to perform the task at a given time or a specific component that is manufactured to perform the task. As used herein, the term 'processor' refers to one or more devices, circuits, and/or processing cores configured to process data, such as computer program instructions.

A detailed description of one or more embodiments of the invention is provided below along with accompanying figures that illustrate the principles of the invention. The invention is described in connection with such embodiments, but the invention is not limited to any embodiment. The scope of the invention is limited only by the claims and the invention encompasses numerous alternatives, modifications and equivalents. Numerous specific details are set forth in the following description in order to provide a thorough understanding of the invention. These details are provided for the purpose of example and the invention may be practiced according to the claims without some or all of these specific details. For the purpose of clarity, technical material that is known in the technical fields related to the invention has not been described in detail so that the invention is not unnecessarily obscured.

Figure 1A:
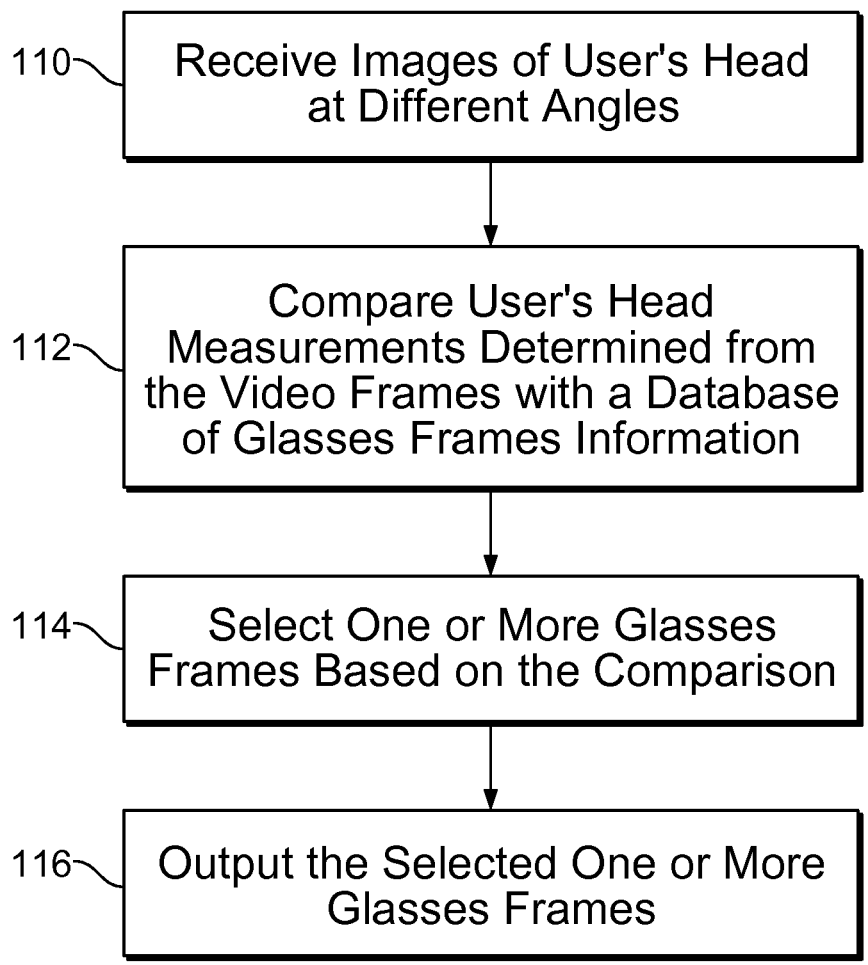
FIG. 1A is a flow chart illustrating a method for selecting glasses frames that fit a user's head.

FIG. 1A is a flow chart illustrating a method for selecting glasses frames that fit a user's head. At step 110, images are received of the user's head at different angles. In some embodiments, at 110, a video or a plurality of video frames of the user's head is received. At step 112, the user's head measurements determined from the images are compared to a database of glasses frame information. In some embodiments, at step 112, the user's head measurements are determined from a video or a plurality of video frames. At step 114, one or more glasses frames are selected from the database of glasses frame information based at least in part on the comparison. At step 116, the one or more selected glasses frames are outputted.

Figure 1B:
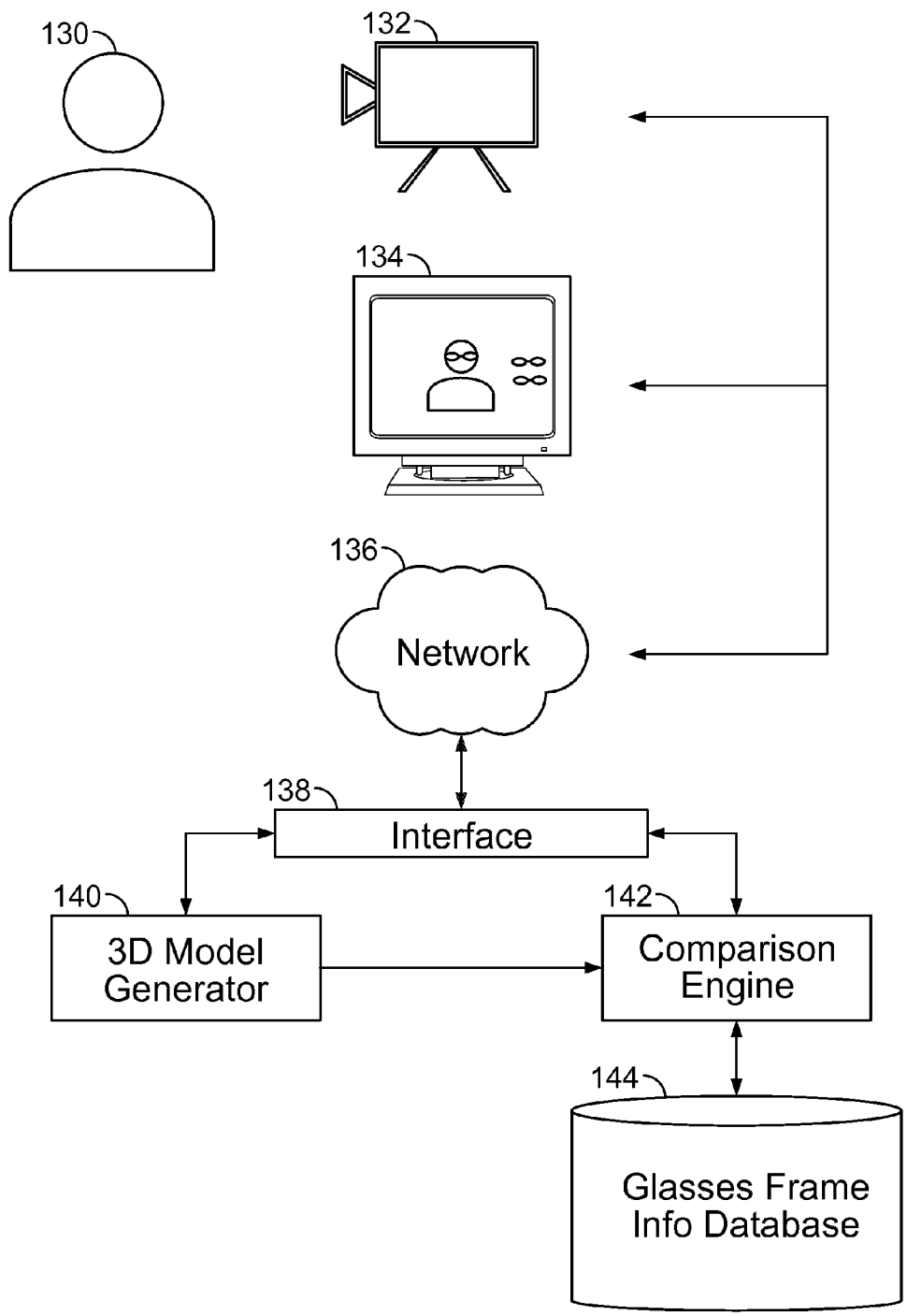
FIG. 1B is a diagram illustrating an example of a system for selecting glasses frames that fit a user's head.

FIG. 1B is a diagram illustrating an example of a system for selecting glasses frames that fit a user's head. User 130 is in front of a camera 132 or webcam in communication with a processor that is running an application that captures video frames and/or images of the user's head. In some embodiments, the captured video frames and/or images are transferred through a network 136 (e.g., WIFI, 3G or local area network). An interface 138 receives the video frames and/or images. In some embodiments, the application capturing the video frames/images or fitting glasses to the user, or portions of the application, is executed on one or more processors and can be located at the client or on the server or a combination of the client and server.

The 3D model generator 140 determines the user's head measurements and a three-dimensional (3D) model from the video/images received of the user's head at different angles. The 3D model may include one or more of the following: images/video frames of the user's head, reference points on the user's head, user head measurements, and a set of rotation/translation/scaling matrices. In some embodiments, the 3D model contains only reference points associated with the user's head. In some embodiments, an initial 3D model is first obtained from a subset of the received video frames/images.

Then the initial 3D model can be adjusted into an adjusted 3D model using an iterative algorithm incorporating additional information from the received video frames/images.

In some embodiments, the images are captured at the client computer and sent over the internet to a server to process the images and create a 3D model of the user's head. In some embodiments, the client computer can create the 3D model of the user's head and send the 3D model over the internet to select glasses that fit the user. Other embodiments with different tasks being executed by different processors or different locations are also included in the scope of this invention. In some embodiments, a scaling reference is captured with the user's head when obtaining video and/or images at step 110 of FIG. 1A. For example, the user is instructed to hold a scaling reference to the user's head and an image is captured of the user with the scaling reference in order to properly scale the user's head measurements and fit glasses frames to the user. In some embodiments, the scaling reference is a measurement in standard units of something in the video frame/image (for example a pupillary distance), is entered by the user. In some embodiments, the camera is calibrated using the video/images captured of the user with the scaling reference.

Comparison engine 142 compares the user head measurements from the 3D model to a database of glasses frame information 144. A penalty function for each of the measurements that factors in fit is used to compare the glasses frame and the user's head measurements. A detailed description of the penalty function is disclosed later in the specification. One or more glasses frames are selected based on a score computed from the penalty function and set thresholds of the score that comprise different levels of fit.

In some embodiments, the outputting of glasses frame information at step 114 of FIG. 1A comprises displaying information associated with one or more glasses frames determined to match a user. In some embodiments, after the user's head measurements are determined, the selected glasses that fit the user are displayed to the user on display 134. In some embodiments, the glasses frame information includes a fit score. In some embodiments the one or more glasses frames determined to match a user are displayed in a list or ordered list associated with the fit score and/or one or more other attributes associated the user and/or the glasses frames in the list. In some embodiments, the at least one of the selected glasses is rendered on an image associated with the user. In some embodiments, at least one of the selected glasses is rendered on a 3D interactive model of the user. This allows the user to visualize how the user looks with a selected pair of glasses. In some embodiments, this allows the user to more easily decide to purchase a pair of glasses without having to visit a physical store.

Figure 2A:
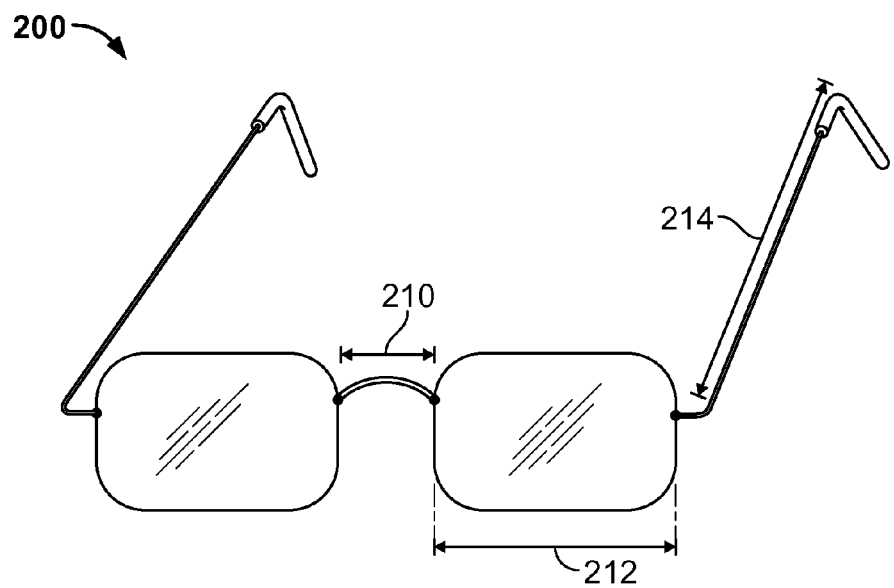
FIG. 2A is a diagram illustrating an example of relevant measurements of a glasses frame.

FIG. 2A is a diagram illustrating an example of relevant measurements of a glasses frame. Glasses frame 200 is measured to obtain relevant distances of a glasses frame. In some embodiments, the relevant distances are bridge length 210, lens diameter 212, and temple distance 214. The bridge length 210 is the distance between the two lenses of the glasses frame. The lens diameter 212 is the diameter of one of the lenses. The temple distance 214 is the length of the glasses frame arm from the corner of the lens to the bend on the temple tips, which goes over the user's ear. In other embodiments, other distances can be measured from the glasses frames. In various embodiments, other ways of expressing the distances, for example, positions of endpoints of each of the distances in a 3D coordinate system, length and offset from a common origin, or an array of points representing each line of the glasses can be stored.

Figure 2B:
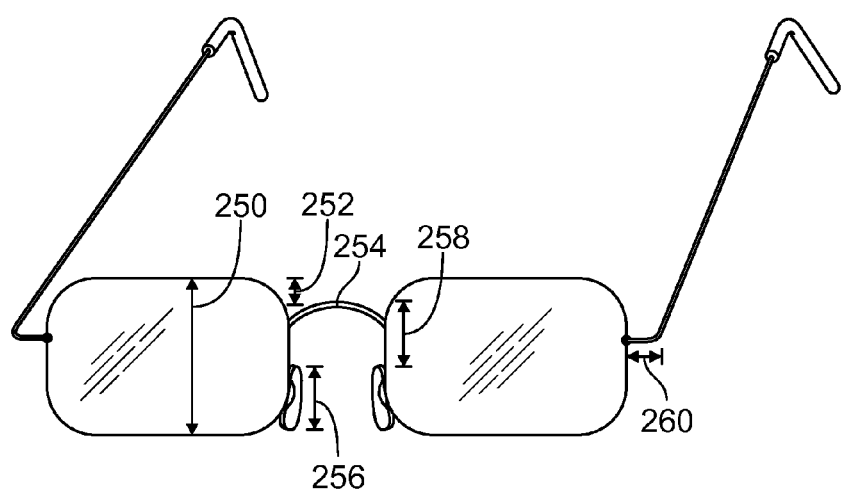
FIG. 2B is a diagram illustrating an example of other relevant measurements of a glasses frame.

FIG. 2B is a diagram illustrating an example of other relevant measurements of a glasses frame. Other relevant measurements of the glasses frame comprise lens height 250, vertical lens offset 252, bridge apex position 254, bridge height, nosepad length and position 256, nosepad vertical offset 258, end piece offset and end piece length 260.

The measurements of the glasses frames comprise a portion of the glasses frame information stored in a database. In some embodiments, glasses frames are measured and the measurements are stored in a database. In some embodiments, a 3D model of each glasses frame is stored in the database. In some embodiments, the glasses frames are scanned with a 3D imager and are stored in the database. In some embodiments, other glasses frame information is stored in the database, including one or more of the following: glasses frame measurements, identifier, name, picture, manufacturer, model number, description, category, type, glasses frame material, brand, part number, and price.

Figure 3:
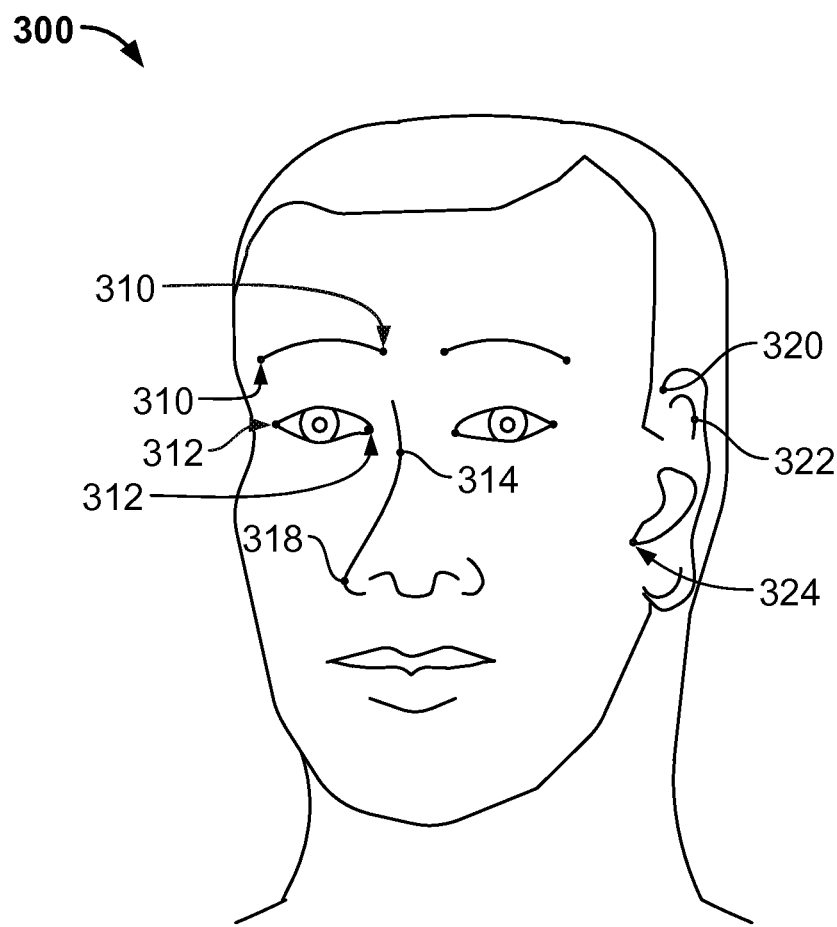
FIG. 3 is a diagram of an example set of reference points on a user's head.

FIG. 3 is a diagram of an example set of reference points on a user's head 300. The reference points are used to determine user head measurements. For example, the endpoints of the user's eyebrow 310, endpoints of the user's eye 312, bridge of the user's nose 314, tip of the user's nose 318, the top point where the helix (the rounded top edge of the ear) joins the head 320, the middle of the antihelix 322 (the flatter lump inside of the helix of the ear), and the bottom of the user's intertragus notch 324 are the reference points obtained from the video frames and/or images. In some embodiments, the reference points are used in calculating the user's head measurements and are a portion of the 3D model of the user's head. Other reference points and other measurements can be obtained from the video frames and/or images of the user's head. For example, other relevant reference points include the midpoint between the user's eyes, the left and right cheekbones, the highest point of the ear lobe or other reference points on a user's head. In some embodiments, a subset of the reference points listed is used. In some embodiments, other reference points of the user's head are used.

Figure 4A:
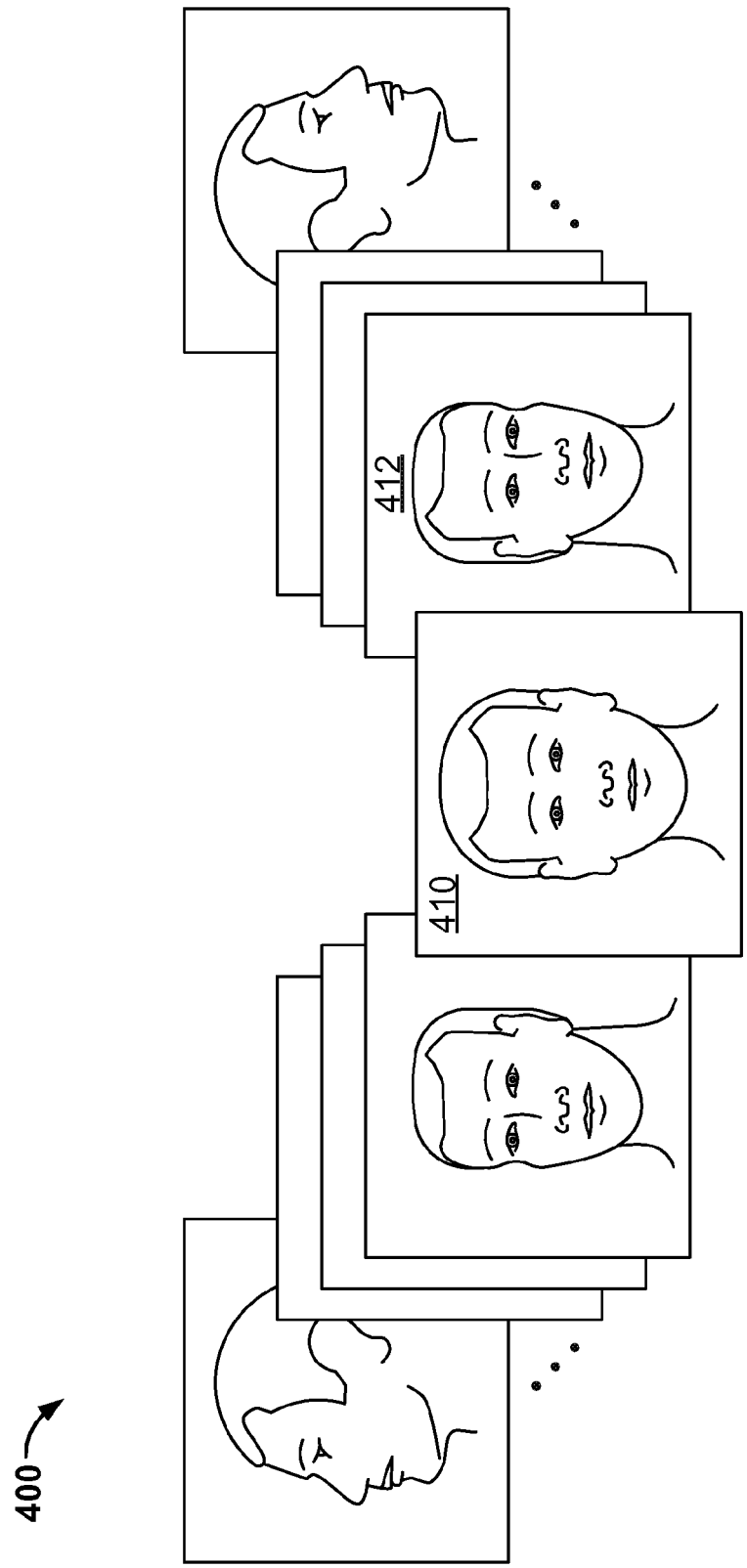
FIG. 4A is an example of received images and/or video frames of the user's head.

FIG. 4A is an example of received images and/or video frames of the user's head. In some embodiments, the user is in front of a webcam and video is captured of the user's head. The user is instructed to turn their head as the camera captures video frames of the user's head. In some embodiments, the user is instructed to look left and then look right. In some embodiments, the user is shown a video clip or an animation of a person turning their head and instructed to do the same. Video frames 400 that were captured and received include at least the user's head at different angles or facing different directions. For example, video frame 410 is an image of the user's head turned at an angle that faces the video camera. Video frame 412 shows the user's head turned at another angle slight to the user's left. The number of video frames captured can vary. The camera can be instructed by a processor to capture the user's head with a continuous video or snapshots (for example, series of images with a delay between captures). In some embodiments, the camera captures images of the user's head in a continuous capture mode, where the frame rate can be lower than capturing a video. The video frames and/or images 400 are then sent to a processor for obtaining user head measurements and fitting to glasses frames. The processor can be local or remote, for example on a server.

Figure 4B:
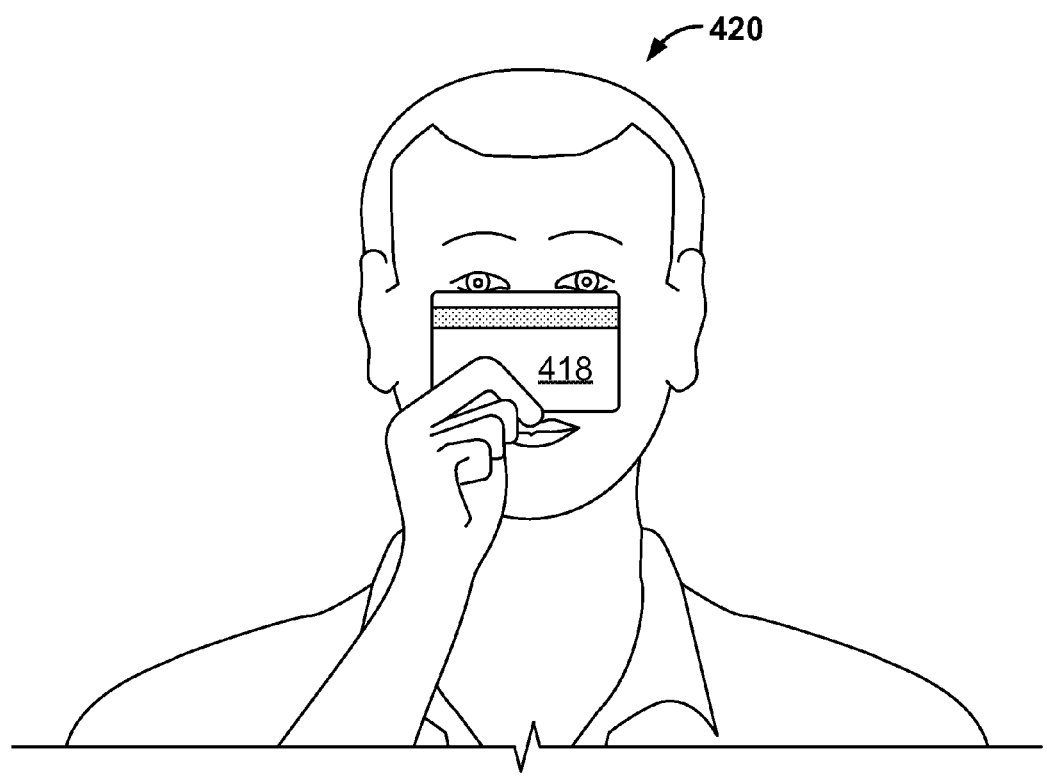
FIG. 4B is an example of a scaling reference needed in order to properly scale the images and/or video frames of the user's head to properly fit the glasses.

FIG. 4B is an example of a scaling reference used at least in part to scale the images and/or video frames of the user's head to properly fit the glasses. For example, a credit card-sized object 418 is held up to the user's head 420 for scaling. During the process of fitting glasses frames to a user, the user is instructed to hold the credit card-sized object to the user's face. A camera or webcam directed at the user can then capture short video or an image of the user with a credit card next to their face. In some embodiments, the credit card-sized object is held on or near various places, for example the bridge of the user's nose. In some embodiments, the scaling reference is a measurement in standard units of something in the video frame/image (e.g., a pupillary distance) and is provided by the user. In some embodiments, a different scaling reference object with a standard and known measurement is used. For example, a coin (e.g., a quarter) is held next to the user's eye.

Additionally, the short video or the image of the user with a scaling reference object is used at least in part to calibrate the camera. By detecting points on the scaling reference object with a known measurement and image characteristics, a matrix representing camera intrinsic parameters is determined and used to calibrate the camera. The camera intrinsic parameters are found by correlating points on the scaling reference object between different video frames/images of the user with the scaling reference object, and calculating the matrix that represents the camera intrinsic parameters using a camera calibration algorithm.

Figure 5:
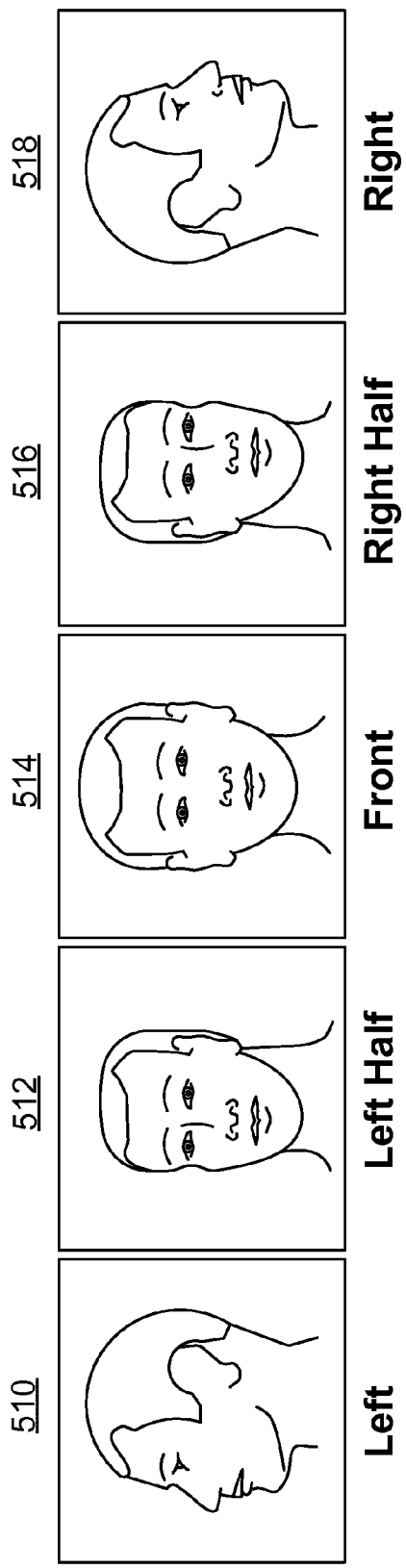
FIG. 5 is a diagram illustrating an example set of orientations used in the process of making an initial 3D model of the user's head and determining user head measurements.

FIG. 5 is a diagram illustrating an example set of orientations used in the process of making an initial 3D model of the user's head and determining user head measurements. The initial 3D model is used in the process of making an adjusted 3D model, from which the user's head measurements are determined. Images/video frames of the user's head are received and then categorized into a set of orientations. For example, a set of orientations used comprises left profile 510, left half 512, front 514, right half 516, and right profile 518. In some embodiments, the set of orientations used comprises left facing, front facing, and right facing. In some embodiments, the set of orientations used comprises one or more of the following: 0 degrees, 45 degrees, 60 degrees, 90 degrees, 120 degrees, 135 degrees, and 180 degrees. By comparing reference points obtained from the images/video frames of the user's head to a model of each of the different orientations, each received image/video frame is categorized into an orientation. In some embodiments, heuristics are used in combination with models of each orientation to categorize the received image/video frames. For example, if the user's right eye is not shown in the image/video frame of the user's head, the image/video frame is categorized as left profile. Or if the user's left eye and only a portion of the user's right eye is in the image/video frame, then the image/video frame is categorized as a left half. Also, for example, if both eyes are seen about equally in the image/video frame, then the image/video frame is categorized as front facing. In some embodiments, a statistical approach is used to categorize the received image/video frames into a set of orientations. Using the statistical approach, the probability of mutual feature positions under different orientations for each image/video frame is calculated and each image/video frame is then categorized into the orientation with the highest probability.

FIG. 6A and FIG. 6B illustrate an example of reference points obtained from a set of image/video frames of the user's head. The reference points are then used to generate an initial 3D model. FIG. 6A shows image/video frame 600, where the user is in the front orientation and reference point 602 is at the inside corner of the user's right eye, which is assigned coordinates (x0, y0). Reference points of the eye may also include inside left eye reference point 604 with coordinates (x1,y1) and outside left eye reference point 606 with coordinates (x2,y2). From the two reference points inside right eye 602 (x2,y2) and inside left eye 604, a bridge distance 608 can be determined. In some embodiments, a lens distance can be determined using inside left eye reference point 604 and outside left eye reference point 606. FIG. 6B shows another orientation, right profile 620, with outside right eye reference point 622 with coordinates (y4, z4) and top point where the helix joins the head reference point 624 with coordinates (y3, z3). From the profile pictures, the z coordinate can be added to the initial 3D model. From the two-dimensional video frames of the user's head, an initial 3D model of the user's head can be determined.

Reference points are obtained from images/video frames of the different orientations. In some embodiments, a best image/video frame for each of the orientations is selected to be used in determining reference points and user head measurements that can be at least in part used to generate the initial 3D model, as shown in FIGS. 6A and 6B. For example, the best image/video frame out of the front orientation is the image/video frame in the front facing orientation with the maximum distance between the endpoints of the eyes. For example, the image/video frame with the largest distance between the right eye and the right ear is determined as the best right profile. Other embodiments for the selection of the best image/video frames include machine learning or various heuristics for certain models that best fit a certain orientation.

FIG. 6C is a diagram illustrating an embodiment of the initial 3D model comprising a set of reference points. In some embodiments, reference points from the 2D images/video frames are combined to make the 3D model of FIG. 6C. The corresponding reference points are combined to make a set of (x,y,z) coordinates representing the position of each of the reference points on the user's head. For example, the (x,y) coordinates of the outside corner of the right eye 612 from the front orientation video frame 600 could be combined with the z coordinate of the outside right eye reference point 622 in the right orientation image/video frame 620 to obtain the reference point 644 with coordinates (x4, y4, z4). The set of (x,y,z) coordinates comprise a portion of the initial 3D model. As shown in the dashed lines of FIG. 6C, the points in the initial 3D model, can be used to generate a representational image of a user's face.

In some embodiments, the initial 3D model comprises an average of reference points in 3D space from a set of users. Using a set of users instead of just the user's face, a generic face is used as the initial 3D model. Instead of generating the initial 3D model from the reference points of the user's head, the generic 3D model is used as a starting point and then adjusted. In some embodiments, the generic 3D model does not include the user's reference points, but is from previous users of the system and/or a predetermined generic model. In some embodiments, the reference points from the user's head are averaged with other users to at least in part generate an initial 3D model.

Figure 7:
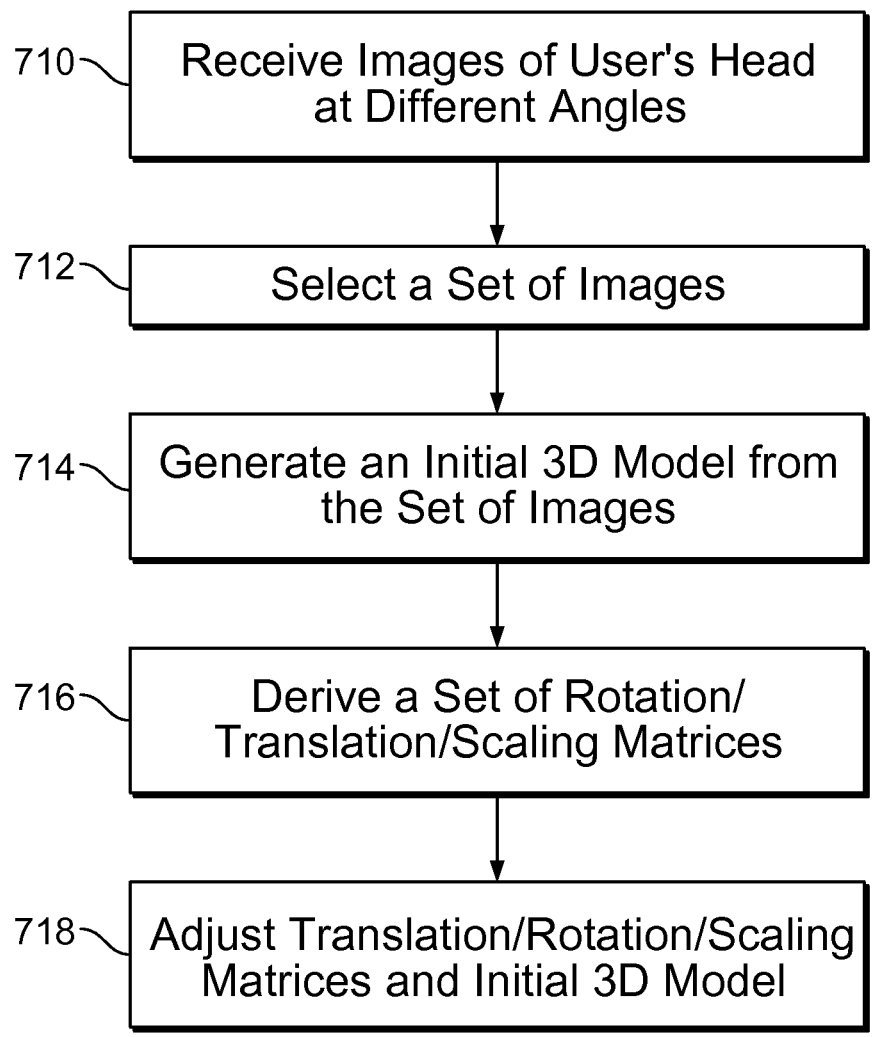
FIG. 7 is a flowchart illustrating an embodiment of a process for adjusting the initial 3D model into an adjusted 3D model to be used in the comparison and the fitting.

FIG. 7 is a flowchart illustrating an embodiment of a process for adjusting the initial 3D model into an adjusted 3D model to be used in the comparison and the fitting. In step 710, the images/video frames of a user's head at different angles are received. At step 712, a set of images/video frames are selected. In some embodiments, the selected set of images/video frames is the best image/video frame from each of the different orientations. At step 714, the initial 3D model is generated from the set of video frames. The initial 3D model comprises a set of (x,y,z) coordinates in 3D space. At step 716, a set of rotation/translation/scaling matrices are derived that transform the initial 3D model into the 2D coordinates in each of the images/video frames. In effect, the rotation/translation/scaling matrix will project, flatten, and scale the initial model described in 3D space into 2D space, which should match the reference points in the 2D image/ video frame of the user's head. Therefore, there will be a rotation/translation/scaling matrix for each image/video frame. Then at step 718, the rotation/translation/scaling matrices are adjusted. An adjusting algorithm is used to iteratively adjust each rotation/translation/scaling matrix and the coordinates of the 3D model. The camera intrinsic parameter matrix is also included during the adjusting. The adjusting algorithm continues until the rotation/translation/scaling matrices transforming each of the received images/video frames converge to a set of coordinates in 3D space that best describe the set of reference points that represent the user's head measurements. This converged set of coordinates comprises an adjusted 3D model that is used for fitting and comparison. Therefore, even if the initial model is the generic face, the 3D model is adjusted to match the reference points from the video frames of the user, which correspond to the specific real-life user's head that glasses frames are to be fitted to. In some embodiments, a bundle adjust algorithm that minimizes reprojection error is used to refine the initial model. In some embodiments, the adjusting algorithm comprises an algorithm that maximizes the likelihood of the received images/video frames parameterized by the 3D model and rotation/translation/scaling matrices. In some embodiments, the user head measurements are calculated from the adjusted 3D model and stored with the 3D model. In some embodiments, the 3D model also comprises the received set of images/video frames of the user's head at different angles and the rotation/translation/scaling matrices. Other information like a user ID or user account information and the resulting selected glasses frames for the user are also included in the 3D model in some embodiments.

Figure 8:
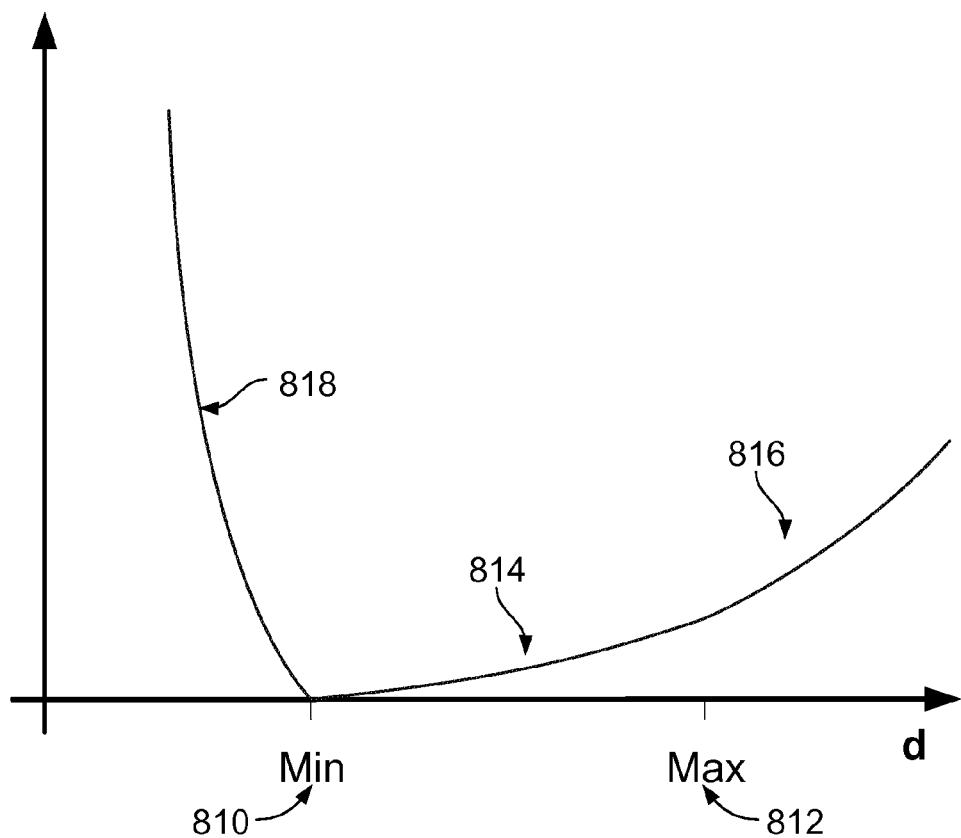
FIG. 8 is an illustration of an example of a penalty function used to evaluate fit of glasses frames.

FIG. 8 is an illustration of an example of a penalty function used to evaluate fit of glasses frames. For example, the penalty function in FIG. 8 could be used to evaluate the bridge length. The x-axis is the distance of the feature being evaluated. The minimum bridge length 810 is the exact distance of the user's bridge and is the ideal bridge length of the glasses frame. The penalty function 818 increases rapidly as the bridge length of the glasses frame gets smaller than the user's bridge distance. For glasses frame's bridge lengths that are larger than the minimum distance and smaller than the maximum bridge distance, the penalty 814 increases at a slower rate. Past the maximum bridge distance, the penalty 816 then increases at a higher rate. In the same way, the other distances, temple distance and lens diameter, are evaluated for a penalty. For the temple distance and lens diameter, the same function or different functions can be used. The penalty function for each of the distances that factor into evaluating fit can also have different shapes, for example, a shifted and flipped step function, a piecewise function, other parabolic functions, or any other appropriate function.

In some embodiments, the penalty functions have a priority. For example, the bridge length penalty may have a higher weight than the temple distance penalty or the lens distance penalty. In some embodiments, the bridge distance penalty is greater than the temple distance penalty, which is greater than the lens distance penalty.

$$P_{d_{bridge}} > P_{d_{temple}} > P_{d_{lens}}$$

In some embodiments, the scale of the y-axis of the penalty function determines the weight of the penalty. In some embodiments, the penalty functions can be normalized and then multiplied with a constant representing their relative weights. Other combinations of penalty function shapes and scaling can also be used to relatively weight the penalty functions.

For each glasses frame compared to the user's head measurements, a score is then calculated using the penalty functions, using a linear combination of weighted penalties. For example, when evaluating one glasses frame with a 15 mm bridge length, if the user's bridge distance is 27 mm, then from the penalty function, the penalty is high, for example 8.5, because the bridge length is much less than the user's bridge distance. The bridge length penalty is then multiplied with its relative weight, which is 1, for the bridge length. In this example, the temple distance has a relative weight constant that is 0.75 and the lens diameter has a relative weight of 0.5. Likewise the temple distance and lens diameter of the glasses frame is evaluated to the user head measurements using a penalty function. Then each of the weighted penalties are added together to create a score. In some embodiments, other distances are factored into the score, e.g., lens height compared to eyebrows and cheekbone positions. In some embodiments, other factors like feedback mechanisms and user reviews are also factored into the score of the glasses frame to the user. In some embodiments, other preferences of the user that are designated by the user, e.g., glasses frame material preferred or glasses frame weight, are factored into the score and make a qualitative fit score for the user.

The scores for the glasses frames are then sorted or ranked in ascending or descending order. For example, the penalties are sorted in ascending order and the glasses frame with the least penalty corresponds to the best fitting. In some embodiments, a threshold is set of a score that indicates that the glasses frame does not fit the user. In some embodiments, other thresholds are also set, for example, a threshold for glasses frames that ideally fit the user, or a threshold for glasses that have a good fit. The thresholds can be set as a numerical constant or as a relative threshold, for example, taking the top 25% of results of glasses that represent a good fit. The scores can also be scaled to be more user-intuitive, like a scale of 1 to 10, to indicate a fit score. Using the scores and thresholds, a set of glasses frames are selected into a results list. In some embodiments, the results list comprises all glasses in the database that fit the user (i.e., all glasses above the "does not fit" threshold). In some embodiments, only the glasses frames that ideally fit the user are selected for the results list. In some embodiments, all of the glasses frames are selected and are associated with a fit score for the user.

FIG. 9 is an illustration of an example of a results list of glasses frames outputted to be displayed. In some embodiments, the results list is displayed in a web browser. The list of results shows a picture of the glasses frame 910, name of the glasses frame 912, price of the glasses frame 914, and the fit score 916. The list is ordered in descending order based on fit score. The fit score is on a scale of 1 to 10 for better user intuitiveness. Other glasses frame information can also be outputted to be displayed, for example, glasses frame measurements, identifier, name, picture, manufacturer, model number, color, description, category, type, glasses frame material, brand, part number, and price. In some embodiments, the list of results is further narrowed and filtered according to user preferences. In some embodiments, the glasses fitting method and system can be embodied as an API (Application Programming Interface) and the selected glasses are outputted to other web applications, for example, used in a search of an online glasses frame seller to display only glasses frames that fit the user. In some embodiments, the selected glasses are sent to a display to be rendered on a 3D model of the user's head. The 3D model of the user's head is also interactive and the user can interact with the model and see how the glasses may look on the user. In some embodiments, the adjusted 3D model of the user's head and results list of selected glasses and associated scores of each of the glasses frames compared to the user are stored in a database for further use. For example, a user seeking glasses saves the results list and shares the results list and model with friends through a link or an account, to get another friend's opinion. In some embodiments, the results list and 3D models are used to allow other people to buy glasses for another person on the internet, or fit another person to glasses who cannot visit a physical store.

Although the foregoing embodiments have been described in some detail for purposes of clarity of understanding, the invention is not limited to the details provided. There are many alternative ways of implementing the invention. The disclosed embodiments are illustrative and not restrictive.

What is claimed is:

1. A system for fitting glasses frames to a user, comprising: a processor configured to:
    compare user head measurements determined from a set of images with at least some of a plurality of sets of glasses frame measurements to generate fit scores corresponding to respective ones of at least a subset of the plurality of sets of glasses frame measurements, wherein the set of images corresponds to a user's head at one or more orientations, wherein to generate a fit score comprises to:
        compare a first feature distance to a corresponding first user head measurement to obtain a first penalty;
        compare a second feature distance to a corresponding second user head measurement to obtain a second penalty;
        determine a penalty value based on the first penalty weighed by a first weight and the second penalty weighed by a second weight, the first weight being different from the second weight; and
        generate the fit score based on the penalty value;
    select a glasses frames corresponding to a set of glasses frame measurements from the plurality of sets of glasses frame measurements based at least in part on the fit scores; and
    display information associated with the selected glasses frames; and
a memory coupled to the processor and configured to provide the processor with instructions.

2. The system of claim 1, wherein an image of the set of images comprises an image selected from at least two recorded images corresponding to the user's head at one orientation of the one or more orientations.

3. The system of claim 1, wherein the processor is further configured to generate a 3D model of the user's head based at least in part on the set of images.

4. The system of claim 3, wherein generating the 3D model of the user's head comprises determining a set of reference points associated with the user's head based at least in part on the set of images.

5. The system of claim 4, wherein generating the 3D model of the user's head further comprises adjusting an initial 3D model based at least in part on the set of reference points associated with the user's head.

6. The system of claim 5, wherein the initial 3D model is determined based at least on references points corresponding to a set of users.

7. The system of claim 3, wherein the user head measurements are determined based at least in part from the 3D model of the user's head.

8. The system of claim 1, wherein a first image of the set of images comprises an image of a scaling reference object of a predetermined size configured to be used to scale a second image of the set of images.

9. The system of claim 1, wherein selecting the glasses frames comprises comparing the fit score corresponding to the glasses frames with a threshold associated with a quality of fit.

10. The system of claim 1, wherein displaying information associated with the selected glasses frames comprises rendering the selected glasses frames over an image of the set of images.

11. The system of claim 1, wherein the one or more orientations are determined by comparing the set of images of the user's head to models of each orientation and categorizing each image as one of the one or more orientations.

12. A method for fitting glasses frames to a user, comprising:
    comparing, using a processor, user head measurements determined from a set of images with at least some of a plurality of sets of glasses frame measurements to generate fit scores corresponding to respective ones of at least a subset of the plurality of sets of glasses frame measurements, wherein the set of images corresponds to a user's head at one or more orientations, wherein the generating of a fit score comprises:
        comparing a first feature distance to a corresponding first user head measurement to obtain a first penalty;
        comparing a second feature distance to a corresponding second user head measurement to obtain a second penalty;
        determining a penalty value based on the first penalty weighed by a first weight and the second penalty weighed by a second weight, the first weight being different from the second weight; and
        generating the fit score based on the penalty value;
    selecting a glasses frames corresponding to a set of glasses frame measurements from the plurality of sets of glasses frame measurements based at least in part on the fit scores; and
    displaying information associated with the selected glasses frames.

13. The method of claim 12, wherein an image of the set of images comprises an image selected from at least two recorded images corresponding to the user's head at one orientation of the one or more orientations.

14. The method of claim 12, further comprising generating a 3D model of the user's head based at least in part on the set of images.

15. The method of claim 14, wherein generating the 3D model of the user's head comprises determining a set of reference points associated with the user's head based at least in part on the set of images.

16. The method of claim 15, wherein generating the 3D model of the user's head further comprises adjusting an initial 3D model based at least in part on the set of reference points associated with the user's head.

17. The method of claim 16, wherein the initial 3D model is determined based at least on references points corresponding to a set of users.

18. The method of claim 12, wherein displaying information associated with the selected glasses frames comprises rendering the selected glasses frames over an image of the set of images.

19. A computer program product for fitting glasses frames to a user, the computer program product being embodied in a non-transitory computer readable storage medium and comprising computer instructions for:
  comparing user head measurements determined from a set of images with at least some of a plurality of sets of glasses frame measurements to generate fit scores corresponding to respective ones of at least a subset of the plurality of sets of glasses frame measurements, wherein the set of images corresponds to a user's head at one or more orientations, wherein the generating of a fit score comprises:
    comparing a first feature distance to a corresponding first user head measurement to obtain a first penalty;
    comparing a second feature distance to a corresponding second user head measurement to obtain a second penalty;
    determining a penalty value based on the first penalty weighed by a first weight and the second penalty weighed by a second weight, the first weight being different from the second weight; and
    generating the fit score based on the penalty value;
  selecting a glasses frames corresponding to a set of glasses frame measurements from the plurality of sets of glasses frame measurements based at least in part on the fit scores; and
  displaying information associated with the selected glasses frames.

20. The system of claim 1, wherein:
  the obtaining of the first penalty is based on a first penalty function; and
  the obtaining of the second penalty is based on a second penalty function.

* * * * *